US008901499B2

(12) United States Patent
Vachon, Jr. et al.

(10) Patent No.: US 8,901,499 B2
(45) Date of Patent: Dec. 2, 2014

(54) MODULAR VAPOR DETECTOR AND IDENTIFIER

(75) Inventors: Kenneth J. Vachon, Jr., Holliston, MA (US); Walter J. Doherty, III, Sharon, MA (US); Leonid Y. Krasnobaev, Framingham, MA (US); Scott E. Miller, Malden, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 286 days.

(21) Appl. No.: 13/474,206

(22) Filed: May 17, 2012

(65) Prior Publication Data

US 2013/0308317 A1 Nov. 21, 2013

(51) Int. Cl.
*G01J 5/02* (2006.01)
*G01N 21/35* (2014.01)

(52) U.S. Cl.
CPC ...... *G01N 21/359* (2013.01); *G01N 2021/3595* (2013.01); *G01N 2201/0221* (2013.01)
USPC ............ 250/339.08; 250/339.05; 250/339.06; 250/339.07

(58) Field of Classification Search
CPC .............. G01N 2021/3595; G01N 2201/0221; G01N 2201/024; G01N 21/359
USPC .................................................... 250/339.08
See application file for complete search history.

(56) References Cited

U.S. PATENT DOCUMENTS

| 2005/0229698 | A1* | 10/2005 | Beecroft et al. ................. 73/300 |
| 2005/0248758 | A1* | 11/2005 | Carron et al. .................. 356/301 |
| 2008/0229805 | A1* | 9/2008 | Barket et al. .................. 73/31.01 |
| 2009/0237647 | A1 | 9/2009 | Azimi et al. |

FOREIGN PATENT DOCUMENTS

EP 2426480 A2 3/2012

OTHER PUBLICATIONS

Anonymous, "Agilent 4100 Exoscan FTIR Spectrometer," http://www.chem.agilent.com/Library/brochures/5990-8097EN_4100-Exoscan-FTIR-Brochure.pdf, May 1, 2011, pp. 1-4.

* cited by examiner

*Primary Examiner* — David Porta
*Assistant Examiner* — Jeremy S Valentiner
(74) *Attorney, Agent, or Firm* — Ion C. Abraham

(57) ABSTRACT

In an embodiment, an apparatus includes a module assembly and a main assembly. The module assembly includes a module assembly housing, a first faceplate and an analysis unit attached to the first faceplate. The main assembly includes a main assembly housing, a second faceplate and an engine unit rigidly attached to the second faceplate. The engine unit generates a light that passes to the analysis unit via a first lens assembly and a second lens assembly. The first lens assembly is attached to the first faceplate and the second lens assembly is attached to the second faceplate. The module assembly when attached to the main assembly causes the first and second faceplates to act as a single mechanical unit that moves independent of movement of the module assembly housing and/or the main assembly housing.

16 Claims, 10 Drawing Sheets

MODULAR VAPOR DETECTOR AND IDENTIFIER

STATEMENT AS TO RIGHTS TO INVENTIONS MADE UNDER FEDERALLY SPONSORED RESEARCH AND DEVELOPMENT

This invention was made with government support under Ordnance Technology Initiative Agreement No. 1 for BRG-011; Ordnance Technology Base Agreement No. 2009-396 awarded as part of the Ordnance Technology Initiative Agreement with Picatinny Arsenal. The government has certain rights in the invention.

BRIEF DESCRIPTION OF THE DRAWINGS

The accompanying drawings, which are incorporated in and constitute a part of this specification, illustrate one or more embodiments described herein and, together with the description, explain these embodiments. In the drawings.

DETAILED DESCRIPTION

The following detailed description refers to the accompanying drawings. The same reference numbers in different drawings may identify the same or similar elements. Also, the following detailed description does not limit the invention.

Figure 1:
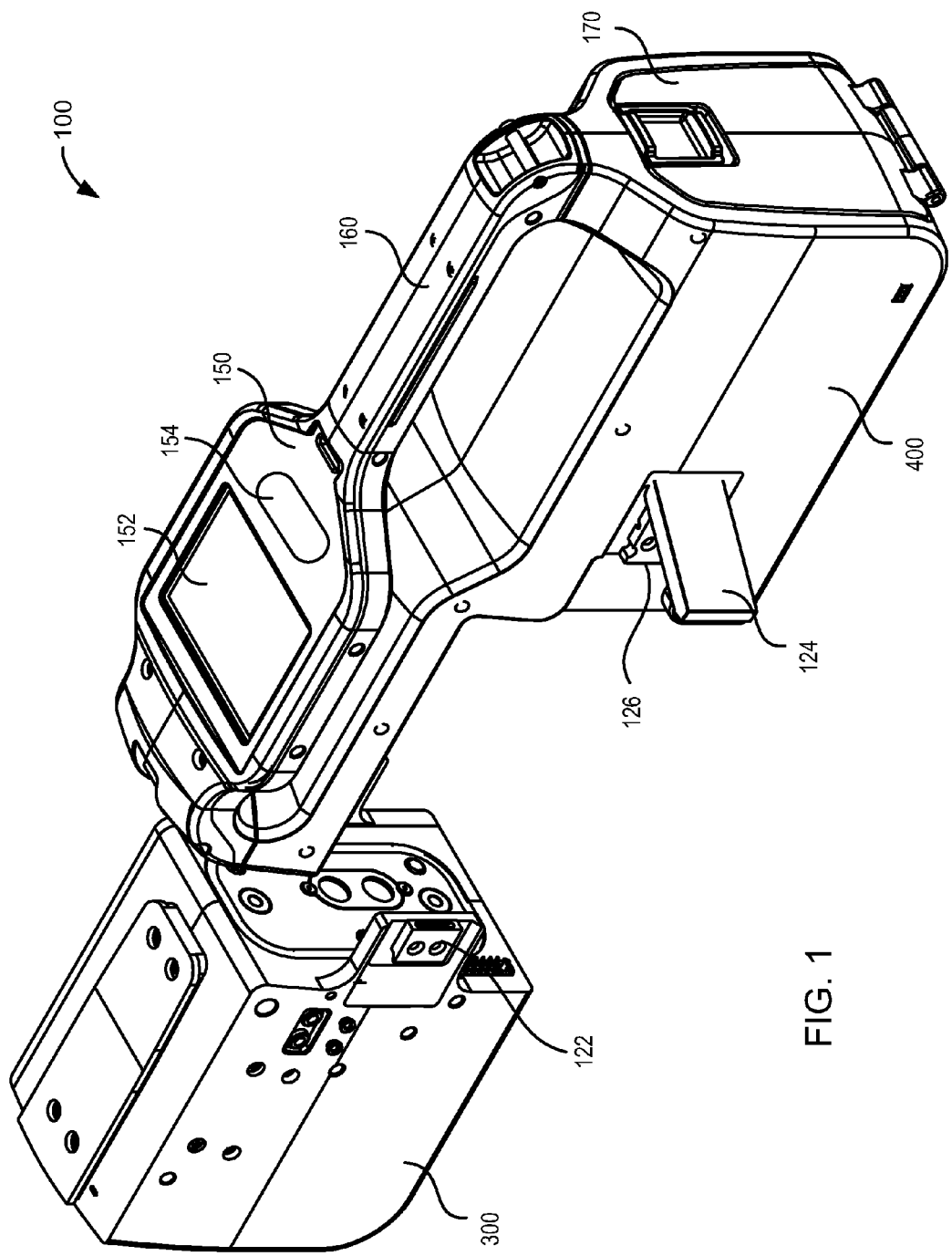
FIG. 1 illustrates a first view of an example of a modular vapor detector and identifier (MVDI)

FIG. 1 illustrates a first view of an example of a modular vapor detector and identifier (MVDI) 100. Referring to FIG. 1, the MVDI 100 may be a handheld Fourier-transform infrared (FTIR) spectrometer that may include a main assembly 400 and a module assembly 300. Embodiments of module assembly 300 may be interchangeable and swapped according to the needs of a user of the MVDI 100.

Multiple chemical analyses on various forms of matter, including airborne vapors, aerosols, emulsions, volatile liquids or powders, stable liquids and powders, and solids, may be performed by MVDI 100 by attaching an appropriate module assembly 300. FTIR spectra associated with the matter may contain features related to specific vibrational and rotational transitions of compounds contained in the matter. This chemical-specific information may be used as a "fingerprint" that may be used to selectively identify the compounds and quantitate amounts of the compounds that may be present in the matter.

The main assembly 400 may include an interface/display unit 150, a handle 160, a lever 124, a base 126, and a battery compartment 170. The interface/display unit 150 may include an output device 152 and an input device 154. The output device 152 may include an interface for outputting information from the MVDI 100. The information may be related to, for example, analysis performed by the MVDI, operational information (e.g., operation menus), and/or other information. The output device 152 may include a liquid crystal display (LCD) device, light-emitting diode (LED) display device, and/or some other display device that may be used to display the information.

The input device 154 may include an interface for inputting information into the MVDI 100. The information may include, for example, menu selections, data, and/or other information that may be input into MVDI 100. The input device 154 may include buttons, membrane switches, keys, a touch pad, a keyboard, and/or other devices that may be used to input the information.

Handle 160 may be used to make MVDI 100 a portable hand-held unit. The handle 160 may be positioned on the main assembly 400 to make the MVDI 100 a well-balanced unit. For example, the handle may be positioned on the main assembly 400 such that the module assembly 300 attaches to the main assembly 400 under the handle to maintain an overall balance (e.g., prevent the unit from tipping one way or another when handled using the handle) of the MVDI 100 when carried. Battery compartment 170 may include provisions for securing a battery that may be used to provide electric power to the MVDI 100.

MVDI 100 may include provisions for securing (e.g., fastening) the module assembly 300 with the main assembly 400. The provisions may include fastening mechanisms such as, for example, latching mechanisms that may be present on opposite sides of MVDI 100. Examples of latching mechanisms that may be used may include compression latches, draw latches (e.g., draw hook latches), push-to-close latches, pawl latches, and/or other latching mechanisms.

A fastening mechanism may include, for example, a keeper 122, a base 126, and a lever 124. The base 126 may be used to attach the lever 124 to the main assembly 400. Lever 124 may attach to keeper 122 to secure module assembly 300 with main assembly 400. Keeper 122 and base 126 may be keyed to accommodate alignment between keeper 122 and base 126.

Figure 2:
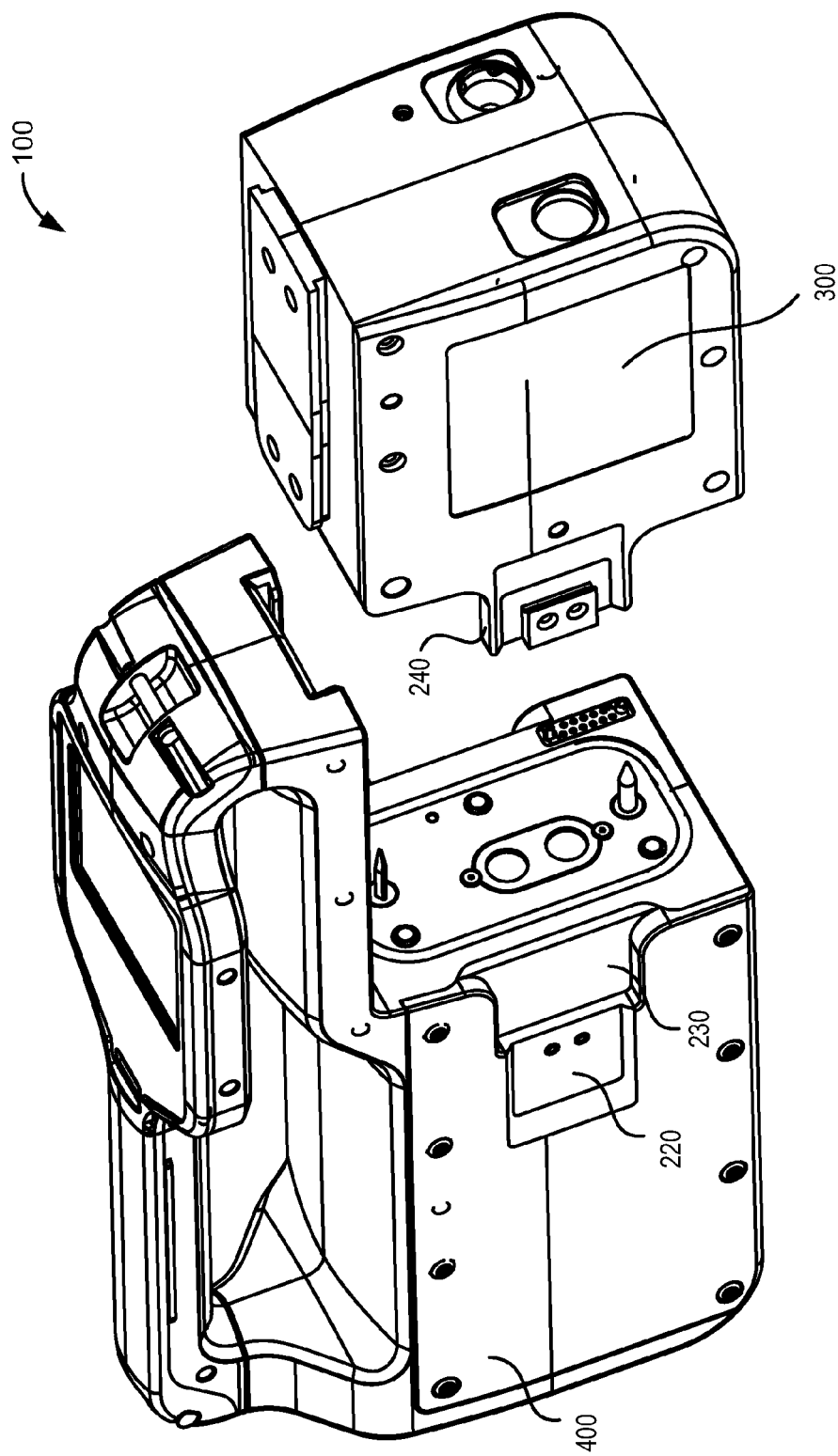
FIG. 2 illustrates a second view of the MVDI.

FIG. 2 illustrates a second view of MVDI 100. Referring to FIG. 2, the main assembly 400 may include a landing area 220 for securing base 126 to the main assembly 400. The landing area 220 may be recessed. Channel 230 may provide a coarse guide to align the module assembly 300 with the main assembly 400. The channel 230 may be recessed below the landing area 220. The module assembly 300 may contain a tab 240 that may fit into channel 230. Note that the main assembly 400 may contain separate landing areas 220 and channels 230 on opposite sides. Note also that module assembly 300 may contain tabs 240 on opposite sides.

Figure 3:
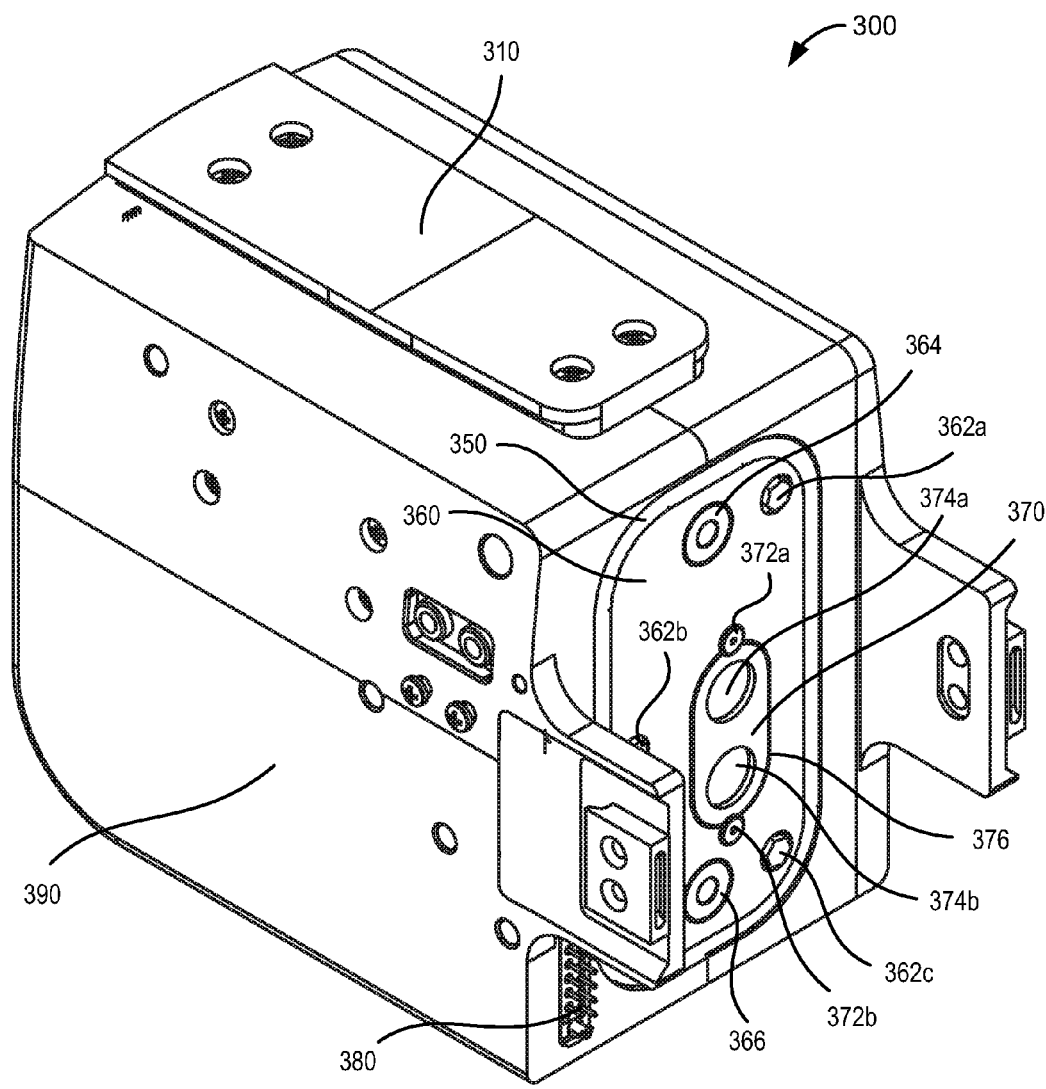
FIG. 3 illustrates a view of an analysis module assembly of the MVDI.

FIG. 3 illustrates a view of the module assembly 300. Referring to FIG. 3, the module assembly 300 may include a key 310, a seal 350, a faceplate 360, a lens assembly 370, an electrical connector 380, and a housing (module assembly housing) 390.

The key 310 may be attached to the housing 390 and may be used for coarsely aligning the module assembly 300 with the main assembly 400. Moreover, the key 310 may provide a rest for the module assembly 300 when the module assembly 300 is attached to the main assembly 400.

The electrical connector 380 may provide a connection for electrical signals that may be transferred between the module assembly 300 and the main assembly 400. The electrical signals may include various digital signals, analog signals, and/or power signals. The power signals may be provided, for example, by a battery that may be contained in the main assembly 400.

Housing 390 may be an assembly that may be used to house contents of the module assembly 300. The housing 390 may be a single piece or may contain multiple pieces. The housing may be made of a lightweight high-impact material (e.g., high-impact plastic) that may accommodate ruggedness and/or portability of the module assembly 300.

The faceplate 360 may contain alignment holes 364 and 366, and hard stops 362a-c. Alignment holes 364 and 366 may be keyed to accommodate alignment pins that may be contained on the main assembly 400. As will be described further below, the alignment holes 364 and 366 may be used in combination with the alignment pins to provide a fine (e.g., precise) alignment between the module assembly 300 and the main assembly 400 when attaching the module assembly 300 to the main assembly 400.

Hard stops 362a-c may provide hard stop limit points of contact with the main assembly 400. Hard stops 362a-c may include bolts that may be rigidly attached to (e.g., bolted in to) the faceplate 360. The bolts may contain rounded smooth heads that may contact similarly positioned flat smooth headed hard stops associated with a faceplate of the main assembly 400. The faceplate of the main assembly 400 will be discussed in more detail below.

Seal 350 may be positioned between the faceplate 360 and the housing 390. Seal 350 may surround faceplate 360 and may be used to prevent contaminants from entering the module assembly 300 via the faceplate 360. Moreover, seal 350 may be pliable to provide mobility for faceplate 360 and enable faceplate 360 to travel independent of the housing 390. Thus, seal 350 may provide mechanical vibration isolation between the faceplate 360 and housing 390.

Module assembly 300 may include an optical port for passing light to and/or from the module assembly 300. The optical port may be implemented using, for example, a lens assembly, such as for example, lens assembly 370. Lens assembly 370 may contain optical windows 374a-b (e.g., lenses) that may enable light (e.g., infrared light) to pass to and from the module assembly 300. The lens assembly 370 may be recessed in faceplate 360. Lens assembly 370 may be surrounded by a seal 376. Seal 376 may be an o-ring seal that may fit in a groove in the lens assembly 370 that accommodates the seal 376.

Lens assembly 370 may be attached to the faceplate 360 using fasteners 372a-b. Fasteners 372a-b may be screws (e.g., flat-head hex screws) that are attached to (e.g., screwed in to) the faceplate 360. Fasteners 372a-b may be recessed in the faceplate 360. Fasteners 372a-b may contain heads that may slightly overlap onto the lens assembly 370 to hold the lens assembly 370 against the faceplate 360.

Figure 4:
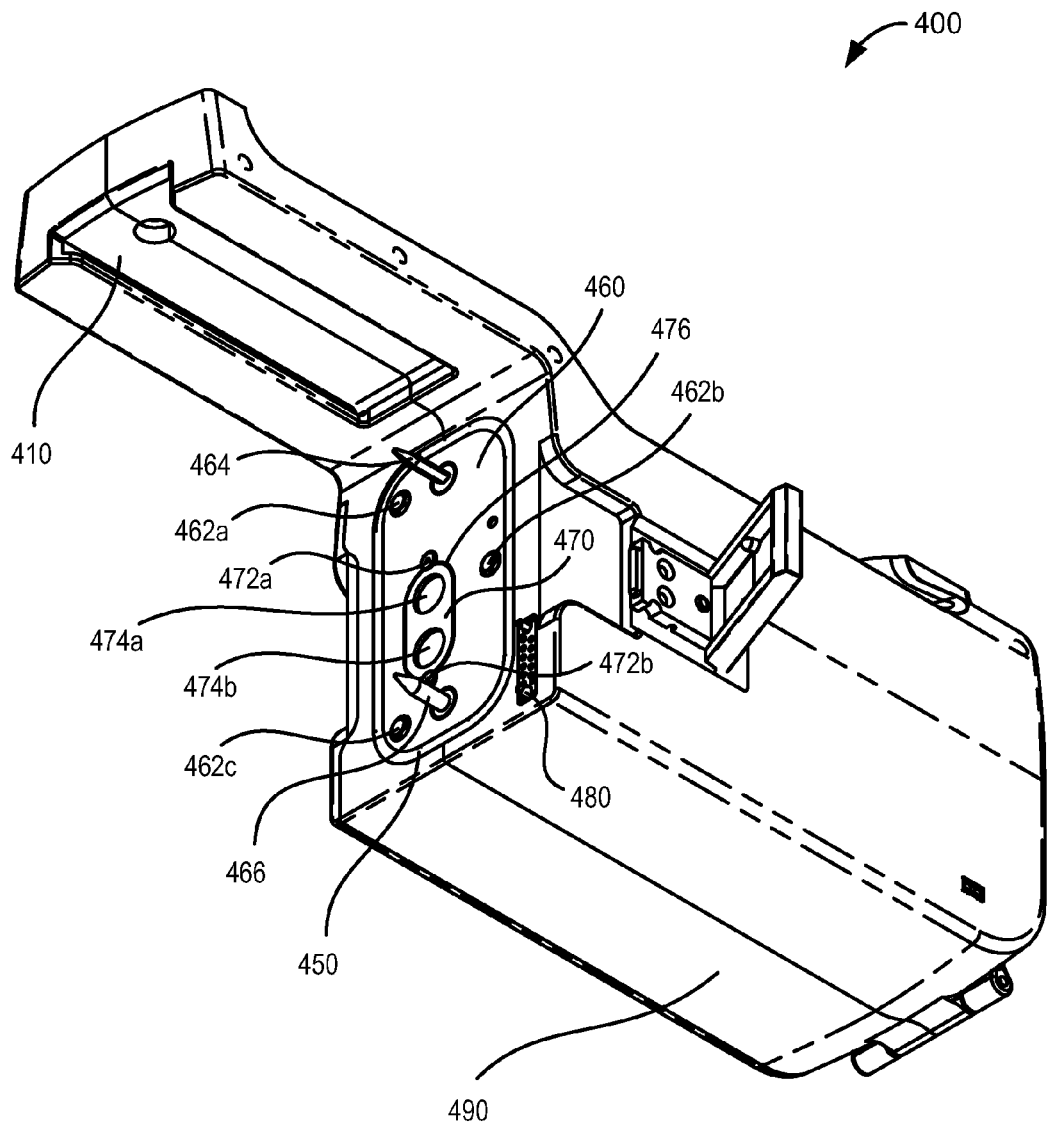
FIG. 4 illustrates a view of a main assembly of the MVDI.

FIG. 4 illustrates a view of main assembly 400. Main assembly 400 may include a guide 410, a seal 450, a faceplate 460, an optical unit 470, an electrical connector 480, and a housing (main assembly housing) 490.

The electrical connector 480 may provide a connection for electrical signals that may be transferred between the module assembly 300 and the main assembly 400. The electrical signals may include various digital signals, analog signals, and/or power signals. The power signals may be provided, for example, by a battery that may be contained in the battery compartment 170 (FIG. 1) of the main assembly 400. Electrical connector 480 may mate with electrical connector 380 when the module assembly 300 is attached to the main assembly 400.

Housing 490 may house contents of the main assembly 400. The housing 490 may be a single piece or may contain multiple pieces. The housing may be made of a lightweight high-impact material (e.g., high-impact plastic) that may accommodate ruggedness and/or portability of the main assembly 400.

The faceplate 460 may contain alignment pins 464 and 466, and hard stops 462a-c. Alignment pin 464 may be a diamond pin that may be relieved to locate, for example, only in one axis. Alignment pin 466 may be a rounded pin that may be relieved to locate, for example, in two axes. Alignment pin 464 may be paired with hole 364 and alignment pin 466 may be paired with hole 366 when module assembly 300 is attached to the main assembly 400. The alignment holes 364 and 366 may be cut to accommodate the shape of pins 464 and 466, respectively, and in conjunction with the pins 464 and 466 provide a fine alignment between the module assembly 300 and the main assembly 400 when attaching the module assembly 300 to the main assembly 400.

Hard stops 462a-c may provide hard stop limit points of contact with the module assembly 300. Hard stops 462a-c may include bolts that may be attached to the faceplate 460. The bolts may contain flat smooth heads that may contact the heads of similarly positioned hard stops 362a-c when the module assembly 300 is attached to the main assembly 400.

Seal 450 may be positioned between the faceplate 460 and the housing 490. Seal 450 may surround faceplate 460. Seal 450 may be used to prevent contaminants from entering the main assembly 400 via the faceplate 460. Moreover, seal 450 may be pliable to provide mobility for faceplate 460 and enable faceplate 460 to travel independent of housing 490. Thus, seal 450 may provide mechanical vibration isolation between the faceplate 460 and housing 490.

Main assembly 400 may include an optical port for passing light to and/or from the main assembly 400. The optical port may be implemented using a lens assembly, such as for example, lens assembly 470. Lens assembly 470 may contain optical windows 474a-b (e.g., lenses) that may enable light to pass to and from the main assembly 400. The lens assembly 470 may be recessed in faceplate 460. Lens assembly 470 may be surrounded by a seal 476. Seal 476 may be an o-ring seal that may fit in a groove in the lens assembly 470.

Lens assembly 470 may be attached to the faceplate 460 using fasteners 472a-b. Fasteners 472a-b may be screws (e.g., flat-head hex screws) that are attached to (e.g., screwed in to) the faceplate 460. Fasteners 472a-b may be recessed in the faceplate 460. Fasteners 472a-b may contain heads that may slightly overlap onto the lens assembly 470 to hold the lens assembly 470 against the faceplate 460.

Figure 5:
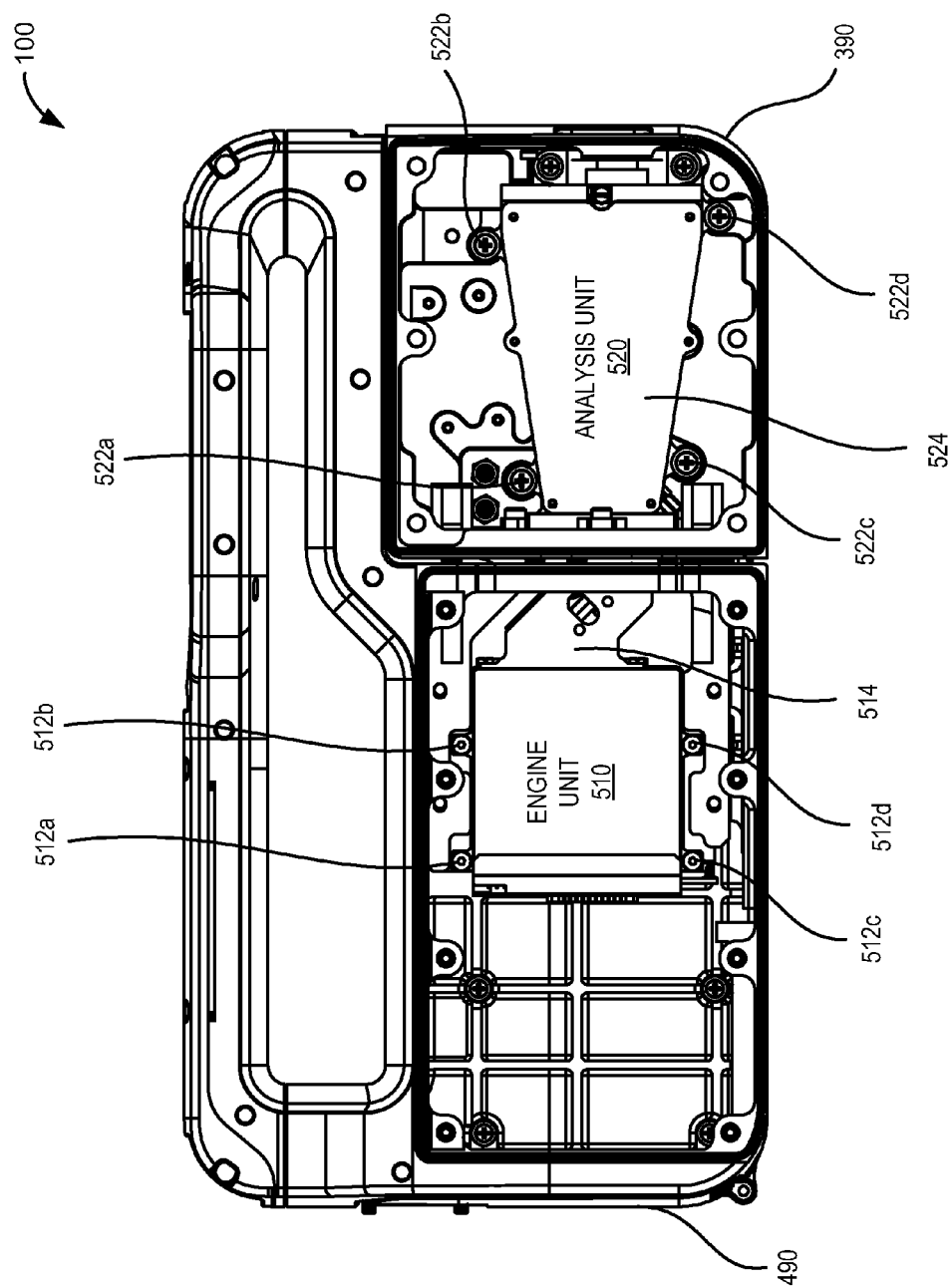
FIG. 5 illustrates a right-side cut-away view of the MVDI.

FIG. 5 illustrates a right-side cut-away view of the MVDI 100. Referring to FIG. 5, the main assembly 400 may include an engine unit 510 and the module assembly 300 may include an analysis unit 520. The engine unit 510 may include, for example, an interferometer which may generate an infrared light source that passes through the analysis unit 520 via lens assemblies 470 and 370. The light source may be attenuated in the analysis unit 520 and the attenuated light source may be returned to the engine unit 510 via the lens assemblies 470 and 370. The engine unit 510 may contain logic (e.g., hardware, software) for detecting and analyzing the attenuated light source and providing one or more results on output device 152 (FIG. 1). The engine unit 510 may also include logic for processing input that may be provided by input device 154.

Engine unit 510 may be enclosed in a housing 514 that may be attached to faceplate 460 (FIG. 4). The housing 514 may be rigidly attached to the faceplate 460 using fasteners (e.g., screws) to make the engine unit 510 and faceplate 460 act as a single mechanical unit. The housing 514 may be attached to the main assembly housing 490 via shock mounts 512a-d to enable the engine unit 510 and faceplate 460 to move as a single mechanical unit whose movement is independent of the movement of the main assembly housing 490.

Likewise, analysis unit 520 may be enclosed in a housing 524 that may be attached to faceplate 360 (FIG. 3). The housing 524 may be rigidly attached to the faceplate 360 using fasteners to make the analysis unit 520 and faceplate 360 act a single mechanical unit. The housing 524 may be attached to module assembly housing 390 via shock mounts 522a-d to enable the analysis unit 520 and faceplate 360 move as a single mechanical unit whose movement is independent of the movement of the module assembly housing 390.

Figure 6:
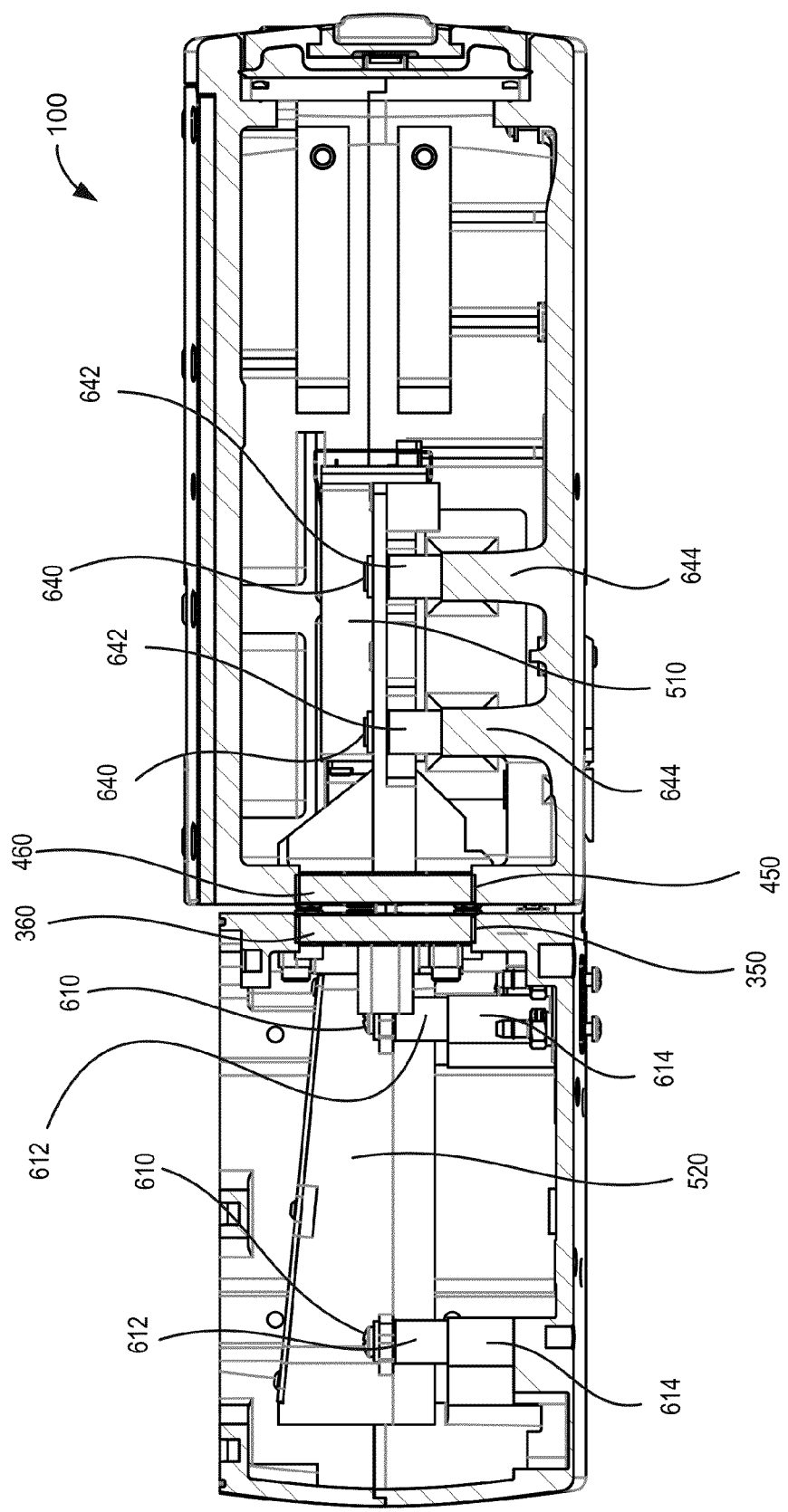
FIG. 6 illustrates a bottom-side cut-away view of the MVDI.

FIG. 6 illustrates a bottom-side cut-away view of the MVDI 100. Referring to FIG. 6, in the module assembly 300, a shock mount 522 may include a stem 614, a shock absorber 612, and a fastener 610. The stem 614 may be made of the same material as the module assembly housing 390 and may be molded as part of the module assembly housing 390. The shock absorber 612 may be made of a pliant material that may be capable of absorbing shock and enable the analysis unit 520 to move independent of the module assembly housing 390. The fastener 610 may be used to secure the analysis unit 520 to the shock mount 522.

In the main assembly 400, a shock mount 512 may likewise include a stem 644, a shock absorber 642, and a fastener 640. The stem 644 may be made of the same material as the main assembly housing 490 and may be molded as part of the main assembly housing 490. The shock absorber 642 may be made of a pliant material that may be capable of absorbing shock and enable the engine unit 510 to move independent of the main assembly housing 490. The fastener 640 may be used to secure the engine unit 510 to the shock mount 512.

Sliding key 310 into guide 410 may provide a coarse positioning of the module assembly 300 and the main assembly 400. Fine positioning may be achieved by aligning pin 464 with hole 364 and pin 466 with hole 366. Attaching the module assembly 300 to the main assembly 400 may include engaging hard stops 362a-c with hard stops 462a-c such that hard stops 362a-c touch respective hard stops 462a-c. The attached module assembly 300 and main assembly 400 may be secured using fastening mechanisms, such as the fastening mechanisms described above.

Attaching the module assembly 300 to main assembly 400 may cause a suitable pressure to be applied to the hard stops 362a-c and 462a-c to make faceplates 360 and 460 act as a single mechanical unit that moves independent of movement of the module assembly housing 390 and/or main assembly housing 490. The pressure may be applied using fastening mechanisms that may be used to secure the attached module assembly 300 with the main assembly 400.

Making the faceplates 360 and 460 act as a single mechanical unit may in turn cause the engine unit 510 and analysis unit 520 to act as a single mechanical unit since the engine unit 510 and analysis unit 520 may be rigidly attached to faceplates 460 and 360, respectively. The engine unit 510 and analysis unit 520 acting as a single mechanical unit in combination with shock mounts 512a-d, 522a-d and seals 350, 450 may enable engine unit 510 and analysis unit 520 to maintain alignment and act independent of the module assembly housing 390 and/or main assembly housing 490. Thus, vibrations that may be produced from either of the housings 390 and 490 may not be coupled to the engine unit 510 and analysis unit 520.

FIGS. 7A-D illustrate block diagrams of example embodiments of MVDI 100. Referring to FIGS. 7A-D, dotted lines show the path of light that travels through the MVDI 100. The main assembly 400 may include engine unit 510 and a battery 710. The battery 710 may be used to provide power for the MVDI 100. Engine unit 510 may include an infrared interferometer that may provide a source for the light. The light may travel from the source into module assembly 300 via lens assemblies 470 and 370. The light may be attenuated in module assembly 300 and the attenuated light may be directed via the lens assemblies 470 and 370 to a detector that may be contained in the engine unit 510.

Figure 7A:
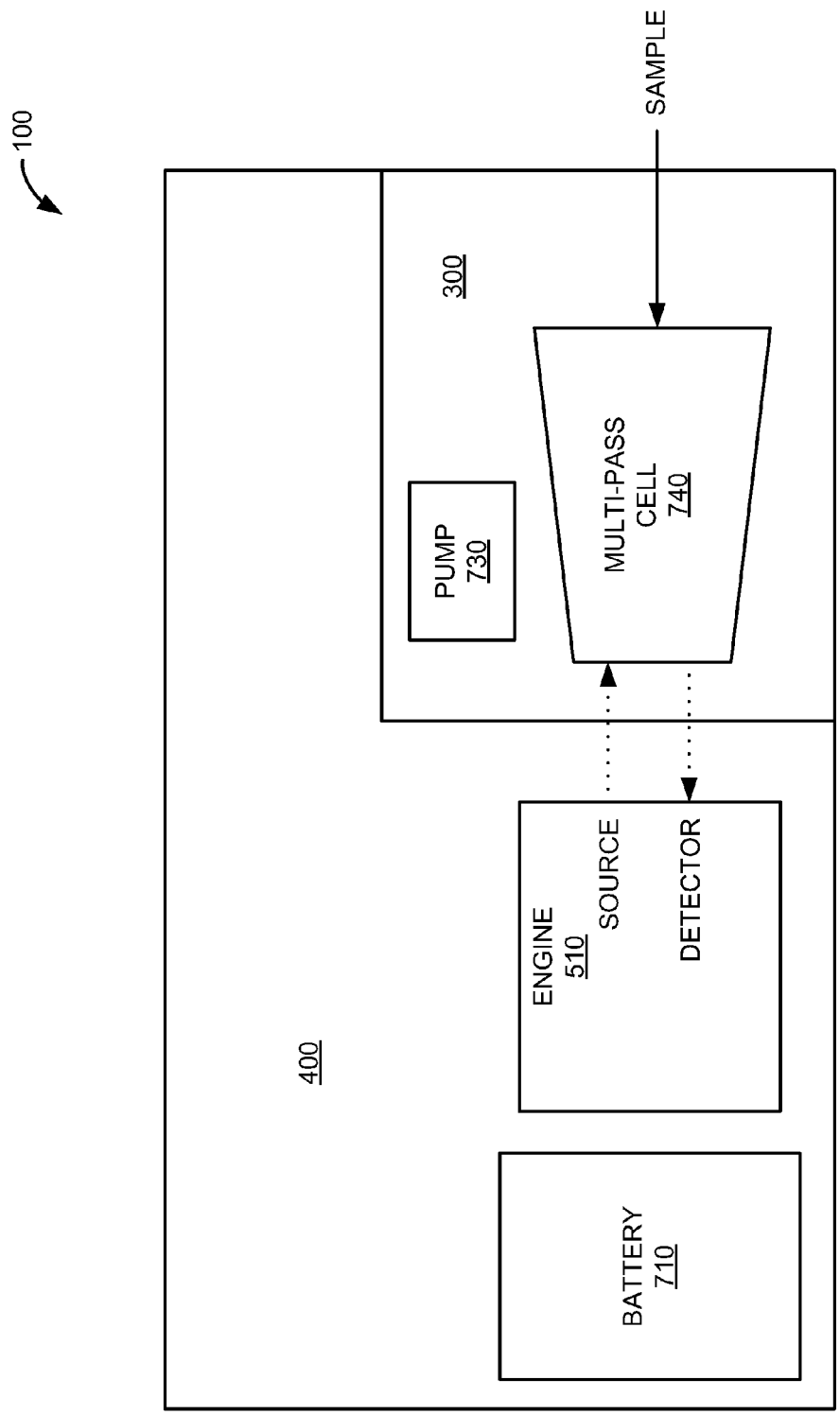
FIGS. 7A-D illustrate block diagrams of example embodiments of the MVDI.

FIG. 7A, shows an example embodiment where the module assembly 300 may include a gas phase spectroscopy cell 740. The gas phase spectroscopy cell 740 may include, for example, a multi-pass, long-pathlength reflective cell, such as a White cell. Cell 740 may be contained in analysis unit 520. After the acquisition of an appropriate background, air or vapor that is to be analyzed may be brought into the cell 740 via active pumping, convection, and/or diffusion. Pump 730 may assist with bringing the air or vapor into the cell 740.

Figure 7B:
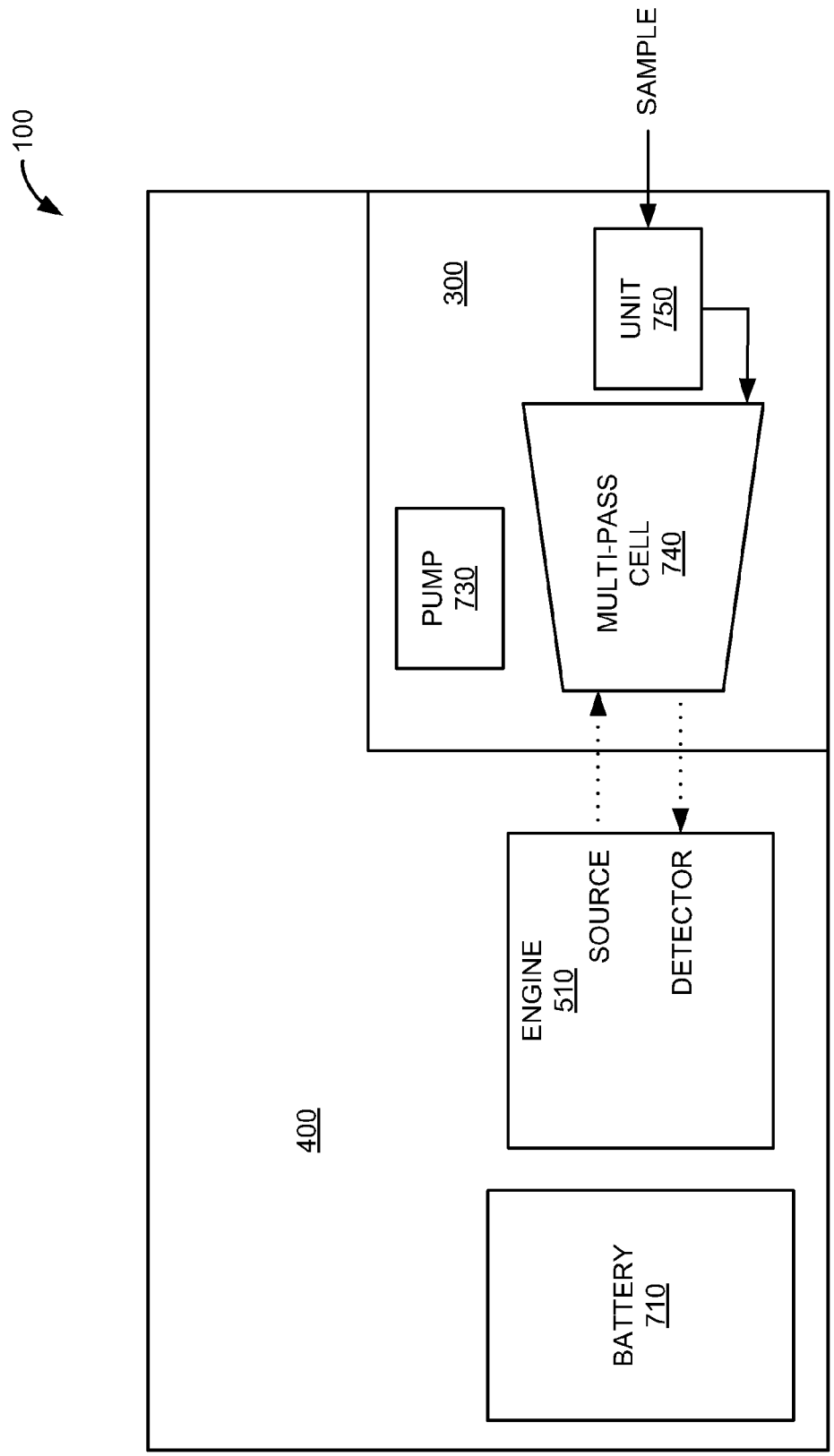

FIG. 7B shows an example embodiment where the cell 740 may be preceded by a unit 750 (e.g., a vapor pre-concentrator, swab heater/desorption unit) that may also be contained in analysis unit 520. Unit 750 may adsorb analyte from a large volume of air or gas. The analyte may then be thermally and/or otherwise eluted into cell 740.

Chemical vapors may be detected and identified at part-per-million levels using the embodiments illustrated in FIGS. 7A-B. While the embodiment shown in FIG. 7A analyzes the ambient environment directly, the addition of unit 750 may decrease a limit of detection by one or more orders of magnitude depending on, for example, a nature of a compound being analyzed.

Figure 7C:
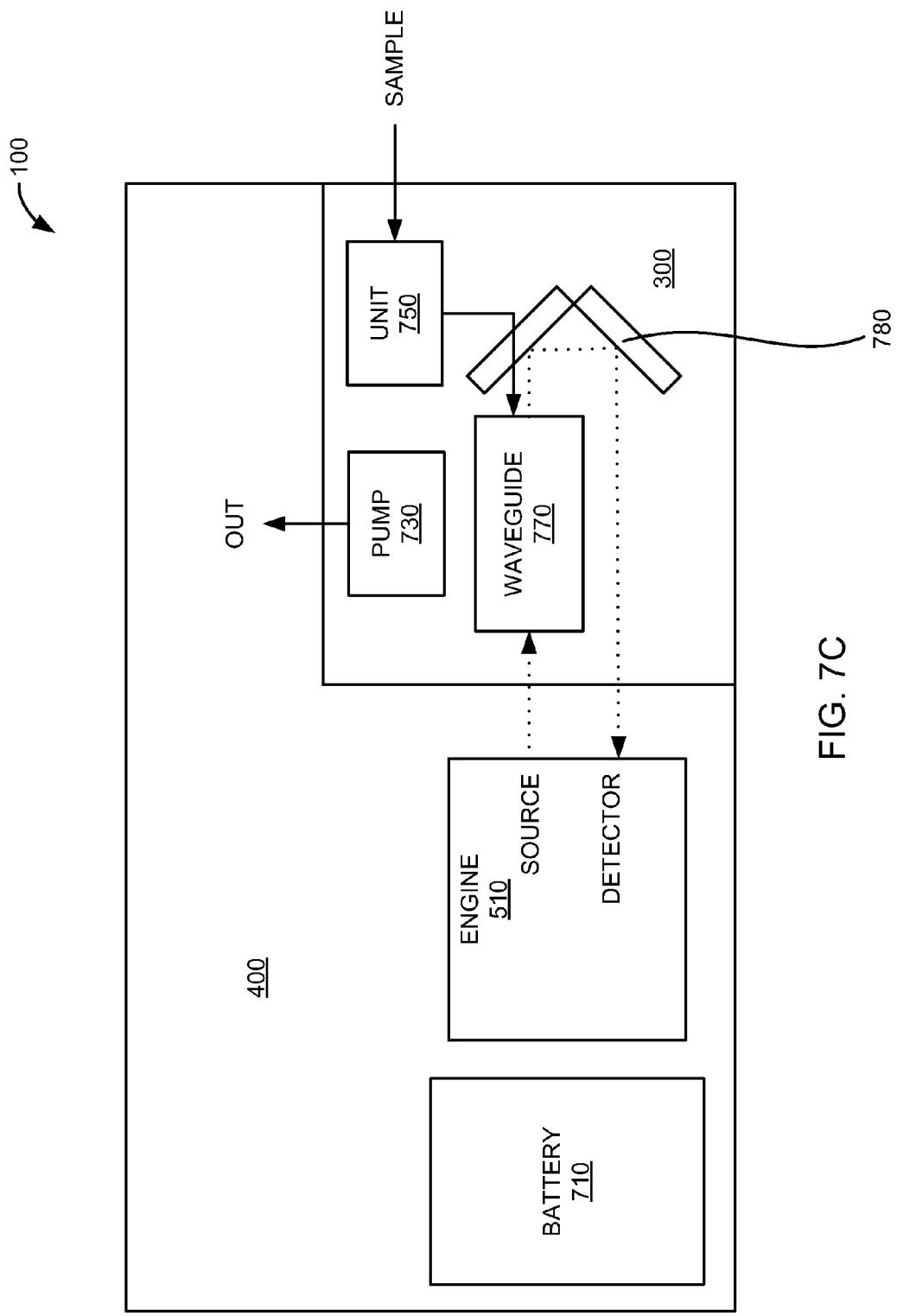

Referring now to FIG. 7C, in cases where a vapor being analyzed may be concentrated into a small volume, or if levels of analyte vapor are relatively high, analysis unit 520 may contain a hollow waveguide 770 that may be used in place of the cell 740. A light reflector 780 (e.g., a mirror) may be also be included in analysis unit 520. The light reflector 780 may be used to reflect the attenuated light to the detector contained in the engine unit 510.

Figure 7D:
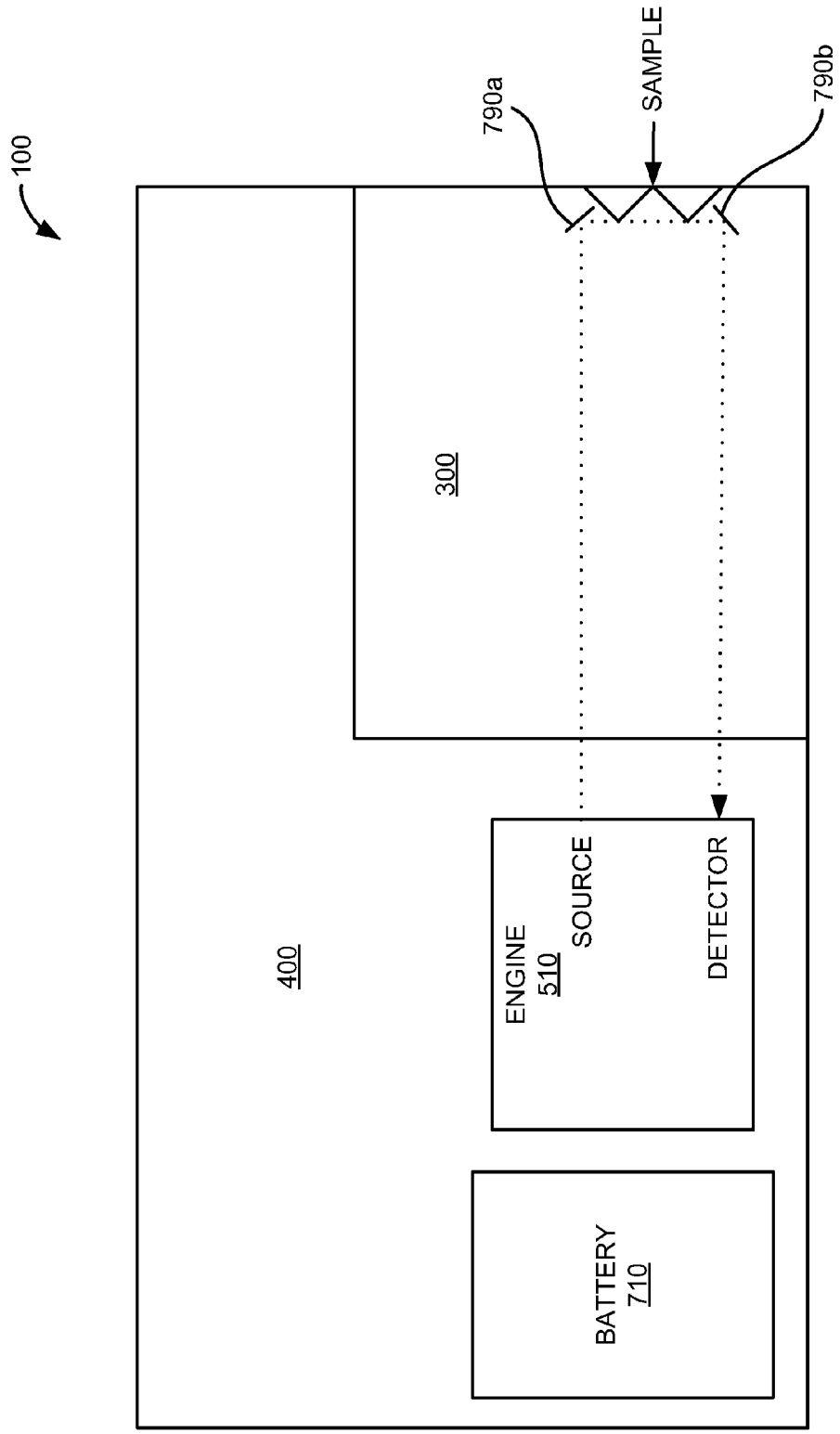

In FIG. 7D, an internal reflection element (IRE) may be included in analysis unit 520 and may be used in place of the cell 740 or waveguide 770. A sample may be pressed directly against the IRE to obtain attenuated total internal reflectance spectra of liquids and solids. The attenuated light may be directed back to engine unit 510 for detection using reflective elements 790a-b, which may be included in analysis unit 520.

It should be noted that in any embodiments described herein, a main assembly may include a spectrometer (such as a Fourier Transform Spectrometer), and the module assembly may include a sample cell. Further, it should be noted that "handheld" may refer to various attributes that may be associated with embodiments described herein. These attributes may include, for example, weight, physical dimensions, and/or power source. For example, being handheld may include an embodiment weighing less than 10 kilograms (kg), and more typically less than 5 kg, 2, 1, or even less than 0.5 or 0.2 kg. Further, being handheld may include an embodiment having dimensions of less than 50 centimeters (cm) or even 30 cm in each dimension, and one of the dimensions (the thickness) may even be less than 10 cm or 5 or 3 cm. In addition, being handheld may include an embodiment being battery powered with the battery typically fitting within the foregoing dimensions and included in the foregoing weights. It should be noted that embodiments described herein may contain provisions to support power from a source other than a battery. For example, a separate power supply may be provided and connected to an embodiment to supply power to the embodiment.

The foregoing description of embodiments is intended to provide illustration and description, but is not intended to be exhaustive or to limit the invention to the precise form disclosed. Modifications and variations are possible in light of the above teachings or may be acquired from practice of the invention.

No element, act, or instruction used herein should be construed as critical or essential to the invention unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

It is intended that the invention not be limited to the particular embodiments disclosed above, but that the invention will include any and all particular embodiments and equivalents falling within the scope of the following appended claims.

What is claimed is:

1. An apparatus comprising:
   a module assembly, the module assembly including:
      a module assembly housing,
      a first faceplate having a first optical port,
      an analysis unit rigidly attached to the first faceplate, the analysis unit configured to receive a sample to be analyzed by the apparatus, the sample attenuating light introduced into the analysis unit via the first optical port; and
   a main assembly, the main assembly including:
      a main assembly housing,
      a second faceplate having a second optical port, and
      an engine unit rigidly attached to the second faceplate, the engine unit generating the light that passes to the analysis unit via the first and second optical ports;
   a first alignment in attached to the second faceplate;
   a second alignment pin attached to the second faceplate;
   a first hole in the first faceplate; and
   a second hole in the first faceplate,
      wherein the first alignment in mates with the first hole and the second alignment pin mates with the second hole when the main assembly is attached to the module assembly.

2. The apparatus of claim 1, wherein the engine unit includes an interferometer that generates the light.

3. The apparatus of claim 1, further comprising:
   one or more shock mounts,
   wherein the one or more shock mounts enable the analysis unit and first faceplate to move as a single mechanical unit independent of movement of the module assembly housing.

4. The apparatus of claim 1, further comprising:
   one or more shock mounts,
   wherein the one or more shock mounts enable the engine unit and second faceplate to move as a single mechanical unit independent of movement of the main assembly housing.

5. The apparatus of claim 1, further comprising:
   a first hard stop attached to the first faceplate; and
   a second hard stop attached to the second faceplate,
      wherein the first hard stop touches the second hard stop when the main assembly is attached to the module assembly.

6. The apparatus of claim 5, wherein the first hard stop includes a head that is rounded and the second hard stop includes a head that is flat.

7. The apparatus of claim 1, wherein the first alignment pin is a diamond pin.

8. The apparatus of claim 7, wherein the second alignment pin is a round pin.

9. The apparatus of claim 1, further comprising:
   a seal that surrounds the first faceplate, the seal providing vibration isolation of the first faceplate from the module assembly housing.

10. The apparatus of claim 9, wherein the seal further prevents contaminates from entering the module assembly.

11. The apparatus of claim 1, further comprising:
    a seal that surrounds the second faceplate, the seal providing vibration isolation of the second faceplate from the main assembly housing.

12. The apparatus of claim 11, wherein the seal further prevents contaminates from entering the main assembly.

13. The apparatus of claim 1, further comprising:
    a lens assembly recessed in the first face plate; and
    a seal that surrounds the first lens assembly.

14. The apparatus of claim 13, wherein the seal is an o-ring seal.

15. The apparatus of claim 1, further comprising:
    a lens assembly recessed in the second face plate; and
    a seal that surrounds the lens assembly.

16. The apparatus of claim 15, wherein the seal is an o-ring seal.

* * * * *